(12) United States Patent
Shirouzu et al.

(10) Patent No.: US 8,664,224 B2
(45) Date of Patent: Mar. 4, 2014

(54) EXTERNAL PREPARATION FOR ATHLETE'S FOOT TREATMENT

(75) Inventors: Toshihiro Shirouzu, Tosu (JP); Youichi Kawamura, Tosu (JP); Hiroki Kawatsura, Tosu (JP); Mitsuhiko Tokunaga, Tosu (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 0 days.

(21) Appl. No.: 13/183,621

(22) Filed: Jul. 15, 2011

(65) Prior Publication Data

US 2011/0269794 A1  Nov. 3, 2011

Related U.S. Application Data

(63) Continuation of application No. 12/338,096, filed on Dec. 18, 2008, now abandoned, which is a continuation of application No. 10/561,499, filed as application No. PCT/JP2004/008992 on Jun. 25, 2004, now abandoned.

(30) Foreign Application Priority Data

Jun. 25, 2003  (JP) ................................. 2003-181264
Dec. 5, 2003  (JP) ................................. 2003-407136

(51) Int. Cl.
  *A61K 31/045* (2006.01)
  *A61K 31/05* (2006.01)
  *A61K 31/137* (2006.01)
  *A61K 31/167* (2006.01)

(52) U.S. Cl.
  USPC ....... 514/254.07; 514/397; 514/646; 514/729

(58) Field of Classification Search
  USPC ............................................ 514/397, 254.07
  See application file for complete search history.

(56) References Cited

U.S. PATENT DOCUMENTS

| | | | |
|---|---|---|---|
| 4,873,265 A | 10/1989 | Blackman | 514/651 |
| 4,945,084 A | 7/1990 | Packman | 514/53 |
| 6,075,056 A | 6/2000 | Quigley et al. | 514/649 |
| 6,133,327 A | 10/2000 | Kimura et al. | 516/8 |
| 6,231,875 B1 | 5/2001 | Sun et al. | 424/401 |
| 6,581,807 B1 | 6/2003 | Mekata | 222/402.1 |
| 2002/0086039 A1 | 7/2002 | Lee et al. | 424/401 |
| 2003/0194445 A1 | 10/2003 | Kuhner et al. | 424/622 |

FOREIGN PATENT DOCUMENTS

| | | |
|---|---|---|
| EP | 0715856 A1 | 6/1996 |
| EP | 1532977 A1 | 5/2005 |
| JP | 03-038522 | 2/1991 |
| JP | 07-223971 | 8/1995 |
| JP | 07-233088 | 9/1995 |
| JP | 08-020527 | 1/1996 |
| JP | 08-151324 | 6/1996 |
| JP | 09-176014 | 7/1997 |
| JP | 10-265377 | 10/1998 |
| JP | 2001-128801 | 5/2000 |
| JP | 2002-284702 | * 10/2002 |
| JP | 2004-035411 | 2/2004 |
| JP | 2004-149508 | 5/2004 |
| WO | WO 99/49835 A1 | 10/1999 |
| WO | WO 01/95718 A1 | 12/2001 |

OTHER PUBLICATIONS

Ali-Shtayeh et al. "Antimicrobial Activity of *Micromeria nervosa* from the Palestinian Area" Journal of Ethnopharmacology 1997 58:143-147.
Encyclopaedia Chimica, Kagaku Daijiten 5 reduced-size edition, Kagaku Daijiten Henshu Iinkai eds., Kyoritsu Shuppan Co., Ltd., Feb. 15, 1987, p. 909.
Database WPI Week 200306—Derwent Publications Ltd., London, GB, AN 2003-060114 and CN 1 368-51 (Tang Y.) Sep. 11, 2002.
*Drugs in Japan*(Ethical Drugs). Ed. Japan Pharmaceutical Information Center, 2000 ($23^{rd}$ Ed.), p. 565.
*Drugs in Japan* (Ethical Drugs). Ed. Japan Pharmaceutical Information Center, 2000 ($23^{rd}$ Ed.), p. 635-637.
*Drugs in Japan* (Ethical Drugs). Ed. Japan Pharmaceutical Information Center, 2000 ($23^{rd}$ Ed.), p. 1622-1623.
Iscan et al. "Antimicrobial Screening of *Mentha piperita* Essential Oils" Journal of Agricultural and Food Chemistry 2002 50:3943-3946.
Kurita et al. "Antifungal Activity of Components of Essential Oils" Agricultural and Biological Chemistry 1981 45(4):945-952.
Maeda et al. "Synthesis and Antifungal Activity of Butenafine Hydrochloride (KP-363), a New Benzylamine Antifungal Agent" Journal of the Pharmaceutical Society of Japan 1991 111(2):126-137.
Pattnaik et al. "Antibacterial and Antifungal Activity of Aromatic Constituents of Essential Oils" Microbios 1997 89:39-46.
Notice of Inquiry issued by the Japanese Patent Office for Japanese Patent Application No. 2005-511050, Oct. 22, 2010, JP.

* cited by examiner

*Primary Examiner* — Lezah Roberts
(74) *Attorney, Agent, or Firm* — Licata & Tyrrell P.C.

(57) ABSTRACT

External preparations for athlete's foot treatment capable of enhancing patient's compliance and capable of reducing the symptom of rubefaction, comprising an anti-trichophyton drug mixed with at least one compound selected from among 1-menthol, menthol analogue compounds and bactericidal compounds.

2 Claims, No Drawings

EXTERNAL PREPARATION FOR ATHLETE'S FOOT TREATMENT

This patent application is a continuation of U.S. application Ser. No. 12/338,096, filed Dec. 18, 2008 now abandoned, which is a continuation of U.S. application Ser. No. 10/561,499, filed Dec. 19, 2005 now abandoned, which is the National Stage of International Application No. PCT/JP2004/008992, filed Jun. 25, 2004, which claims the benefit of priority from Japanese Application No. 2003-407136, filed Dec. 5, 2003 and Japanese Application No. 2003-181264, filed Jun. 25, 2003, teachings of each of which are herein incorporated by reference in their entirety.

TECHNICAL FIELD

The invention relates to an external preparation for athlete's foot treatment, comprising an anti-trichophyton drug and at least one compound, which is selected from 1-menthol, menthol analogue compounds and bactericidal compounds, as an essential ingredient.

BACKGROUND ART

As an anti-fungal agent used for an external preparation for athlete's foot treatment, various antifungal agents such as imidazole, triazole, thiocarbamic acid, benzylamine, allylamine and morpholine types have been developed and have been on the market.

However, each of anti-fungal agents has a difference in its width of the antifungal spectrum and the antifungal activity, and there is no antifungal agent which shows a strong antibacterial activity over *Trychophyton* and other fungi, for example, *Candida albicans* and the like, fungi in general, whereby an external preparation and the like, in which an antifungal activity or the like are strengthened by a combination of two or more of antifungal agents, are reported (ex. see Patent documents 1-3).

In addition, although a composition with a strengthened antifungal activity is also reported, in which an allylamine type antifungal agent and menthol are blended, this increases the activity against so called *Trychophyton* and does not strengthen the antifungal activity against other fungi such as *Candida albicans* (ex. see Patent document 4).

Further, although there are a preparation in which a peripheral vasodilator is added to an antifungal agent (ex. see Patent document 5) and a preparation in which an antifungal agent is added with a substance such as methyl salicylate, glycol salicylate, crotamitone, peppermint oil or 1-menthol to improve a horny layer accumulation of the antifungal agent (ex. see Patent document 6), they do not show any excellent antifungal property against *Trychophyton* and other fungi including *Candida albicans* and the like.

In addition, any external preparation disclosed in the above documents did not suppress the growth of skin habitual bacteria such as *Staphylococus aureus* and did not have effects in a case that the skin habitual bacteria such as *Candida albicans* and *Staphylococus aureus*, which accelerated the discomfort of athlete's foot (itch, bad smell, etc.), grew abnormally, therefore, it could not be said that it satisfactorily enhanced patient's compliance after applying such external preparation described above.

Furthermore, in case of using the above substance improving a horny layer accumulation, a frequency of occurrence of a light symptom such as rubefaction, which an antifungal agent originally has in not a serious degree, is enhanced, whereby further enhancement of patient's compliance has been desired.

Patent document 1: JP, A1, 3-38522
Patent document 2: JP, A1, 9-176014
Patent document 3: JP, A1, 2004-35411
Patent document 4: JP, A1, 2004-149508
Patent document 5: JP, A1, 7-233088
Patent document 6: JP, A1, 8-20527

DISCLOSURE OF THE INVENTION

Problems to be Solved by the Invention

Although an anti-trichophyton drug such as butenafine hydrochloride has a very excellent antifungal action even in alone, the invention provides an external preparation for athlete's foot treatment, having a more excellent effect in points such as enhancement of patient's compliance and reduction of the symptom of rubefaction.

Means to Solve the Invention

After extensive researches to enhance patient's compliance on an external preparation for athlete's foot treatment, the inventors found out that not only *Trichophyton* but also other fungi such as *Candida albicans* and a skin habitual bacteria such as *Staphylococus aureus* are effectively reduced by an external preparation containing an anti-trichophyton drug and at least one compound selected from 1-menthol, menthol analogue compounds and bactericidal compounds as an essential ingredient.

Namely, the invention relates to an external preparation for athlete's foot treatment, comprising an anti-trichophyton drug mixed with at least one compound selected from 1-menthol, menthol analogue compounds and bactericidal compounds.

In addition, the invention relates to the external preparation for athlete's foot treatment, wherein the anti-trichophyton drug and at least one compound selected from 1-menthol, menthol analogue compounds and bactericidal compounds are blended in 0.1-10% by mass and 0.5-5% by mass respectively.

Further, the invention relates to the external preparation for athlete's foot treatment, wherein the menthol analogue compound is 3-1-menthoxypropane-1,2-diol.

The invention relates to an external preparation for athlete's foot treatment, wherein the bactericidal compound is isopropylmethylphenol.

In addition, the invention relates to an external preparation for athlete's foot treatment, wherein the anti-trichophyton drug is selected from benzylamine type, allylamine type, thiocarbamic acid type and imidazole type antifungal agents.

Further, the invention relates to an external preparation for athlete's foot treatment, wherein the anti-trichophyton drug is one kind selected from butenafine hydrochloride, terbinafine hydrochloride, tolnaftate, bifonazole, ketoconazole, neticonazole hydrochloride and lanoconazole.

Furthermore, the invention relates to an external preparation for athlete's foot treatment, wherein the anti-trichophyton drug and 1-menthol are blended.

The invention relates to the external preparation for athlete's foot treatment, wherein butenafine hydrochloride, 1-menthol and isopropylmethylphenol are blended.

In addition, the invention relates to the external preparation for athlete's foot treatment, also comprising at least one kind of a local anesthetic, an antihistamine and an anti-inflammatory drug.

Further, the invention relates to the external preparation for athlete's foot treatment, wherein the local anesthetic is dibucaine hydrochloride, or lidocaine or its salt.

Furthermore, the invention relates to the external preparation for athlete's foot treatment, wherein the antihistamine is chlorpheniramine maleate, or diphenhydramine or its salt.

Further, the invention relates to the external preparation for athlete's foot treatment, wherein the anti-inflammatory drug is glycyrrhetinic acid or its salt, or allantoin.

Further, the invention relates to the external preparation for athlete's foot treatment, wherein butenafine hydrochloride, 1-menthol, dibucaine hydrochloride, chlorpheniramine maleate and glycyrrhetinic acid are blended.

Consequently, in an anti-trichophyton drugs of which antibacterial action against fungi except *Trichophyton* is not necessarily satisfactory, the external preparation for athlete's foot treatment of the invention suppresses the growth of skin habitual fungi such as *Staphylococus aureus* and *Candida albicans*, which become a cause of a bad smell of foot due to athlete's foot, aggravation athlete's foot and the like, without combination of an antifungal agent, and not only improves a therapeutic effect for athlete's foot compared with a case simply to reduce *Trichophyton* but has effect to enhance patient's compliance.

In addition, by blending at least one kind of compound, preferably two kinds of compounds in combination, which were selected from 1-menthol, a menthol analogue compound and a bactericidal compound, it was found that an anti-trichophyton drug could synergistically suppress the growth of *Staphylococus aureus* and *Candida albicans* in a lower blend amount.

Further, if said external preparation for athlete's foot treatment contains at least one kind among a local anesthetic, an antihistamine and an anti-inflammatory drug, it suppresses rubefaction which an anti-trichophyton drug rarely produces even if in a slight degree, and further favorable enhancement of compliance can be obtained. Although this effect can be obtained by blending at least one kind among the local anesthetic, the antihistamine and the anti-inflammatory drug, it is possible to get further favorable effect by combination of two or more kinds.

BEST EMBODIMENT FOR CARRYING OUT THE INVENTION

As described above, in the external preparation for athlete's foot treatment, an anti-trichophyton drug is blended in a specific concentration, that is, 0.1-10.0% by mass, preferably 1-5% by mass, with at least one kind of compound selected from 1-menthol, a menthol analogue compound and a bactericidal compound in the range of 0.5-5% by mass, preferably 1-3% by mass in total.

By making the blend amount of the anti-trichophyton drug not less than 0.1% by mass, the effect as an anti-trichophyton agent can easily be obtained, and even if blending not less than 10% by mass, the effect as the anti-trichophyton agent is hardly improved.

The anti-trichophyton drugs used in the invention are benzylamine type, allylamine type, thiocarbamic acid type and imidazole type and triazole type antifungal agents, specifically, include butenafine hydrochloride, terbinafine hydrochloride, tolnaftate, miconazole, bifonazole, ketoconazole, clotrimazole, econazole nitrate, neticonazole hydrochloride, lanoconazole, isoconazole, oxiconazole, sulconazole, tioconazole, fluconazole and itraconazole, though butenafine hydrochloride, terbinafine hydrochloride, tolnaftate, bifonazole, ketoconazole, neticonazole hydrochloride and lanoconazole are preferable, and butenafine hydrochloride is particularly preferable.

Although butenafine hydrochloride is high in activity against *Trichophyton*, the activity against *Candida albicans* and *Staphylococus aureus* can not be expected much, and therefore, by using it with at least one kind of compound in combination, which are selected from 1-menthol, a menthol analogue compound and a bactericidal compound, preferably the activity against *Trichophyton* as well as *Candida albicans* and *Staphylococus aureus* can synergistically be enhanced.

Compounds used together with the anti-trichophyton drug in the invention include 1-menthol, in addition, menthol analogue compounds such as dl-menthol, 3-l-menthoxypropane-1,2-diol, isopulegol, neoisopulegol, neomenthol, isomenthol, neo-isomenthol, citronellol and linallol, and bactericidal compounds such as isopropylmethylphenol, dequalinium chloride, dequalinium acetate, benzethonium chloride, benzalkonium chloride, chlorhexidine chloride, chlorhexidine gluconate, hinokitiol and resorcin, though 3-l-menthoxypropane-1,2-diol, isopropylmethylphenol and the like are preferably used.

Further, combined use of 1-menthol and isopropyl-methylphenol are particularly preferable.

In addition, by blending at least one kind of compound in not less than 0.5% by mass in total, which are selected from 1-menthol, a menthol analogue compound and a bactericidal compound, the growth of *Candida albicans* and *Staphylococus aureus* can preferably be suppressed, and making it not more than 5% by mass is preferable because a problem of difficult drying in a liquid preparation does not occur.

Although the kinds of antihistamines used in the invention include cholorpheniramine or its salts, diphenhydramine or its salts, promethazine, mequitazine and the like, cholorpheniramine, diphenhydramine or its salts are preferable.

The concentration of the antihistamine is preferably 0.05-5.0% by mass, more preferably 0.05-2.0% by mass. By making the blend amount of the antihistamine not less than 0.5% by mass, the effect as the antihistamine can easily be obtained, and even if making it not less than 5.0% by mass it does not improve the effect as the antihistamine.

Although the kinds of local anesthetics used in the invention include lidocaine or its salts, dibucaine or its salts, tetracaine or its salts, procaine or its salts, ethyl aminobenzoate and the like, dibucaine hydrochloride, or lidocaine or is salts are preferable.

The concentration of the local anesthetic is preferably 0.01-5.0% by mass, more preferably 0.05-2.0% by mass. By making the blend amount of the local anesthetic not less than 0.01% by mass, the effect as the local anesthetic can easily be obtained, and even if making it not less than 5.0% by mass it does not improve the effect as the local anesthetic.

The kinds of anti-inflammatory drugs used in the invention include glycyrrhetinic acid or its salts, non-steroidal types such as methyl salicylate, glycol salicylate, indometacin, diclofenac, felbinac, piroxicam, ketoprofen, ibuprofen piconol, bufexamac or allantoin, and steroidal types such as amcinonide, prednisolone valerate, diflucortolone valerate, dexamethasone valerate, betamethasone valerate, dexamethasone acetate, hydrocortisone acetate, dexamethasone, triamcinolone acetonide, halcinonide, betamethasone dipropionate, fluocinonide, fluocinolone acetonide, prednisolone, deprodone propionate, clobetasol propionate or betamethasone, though glycyrrhetinic acid or its salts, or allantoin are preferable.

The concentration of the anti-inflammatory drug is preferably 0.05-10.0% by mass, more preferably 0.05-2.0% by mass. By making the blend amount of the anti-inflammatory drug not less than 0.05% by mass, the effect as the anti-inflammatory drug can easily be obtained, and even if making it not less than 5.0% by mass it does not improve the effect as the anti-inflammatory drug.

The formula in which dibucaine hydrochloride, cholorpheniramine maleate and glycyrrhetinic acid are blended for an external preparation for athlete's foot treatment consisting of butenafine hydrochloride and 1-menthol is particularly preferable because it can synergistically enhance the compliance.

Further, the external preparation described in the invention includes a liquid preparation, a cream, a lotion, an aerosol preparation, a patch and the like.

The external preparation of the invention may contain a usual base according to its form, and in the case of the liquid preparation or the lotion, a lower alcohol, a polyhydric alcohol, water or the like may be contained.

In the case of the cream, an oily base, a higher alcohol, a fatty acid ester, or a polyhydric alcohol or its derivative, a surfactant, a gellant, water or the like may be contained.

As the aerosol preparation, a lower alcohol, a polyhydric alcohol or the like may be contained to dissolve the drug of the invention.

As the lower alcohol used in the above formulas, methanol, ethanol, denatured ethanol, isopropanol and the like may be illustrated.

As the oily base, liquid paraffin, vaseline, paraffin-wax and the like may be illustrated, and the higher alcohol is $C_{10-20}$ alcohol, preferably cetyl alcohol, stearyl alcohol, cetostearyl alcohol and oleyl alcohol are preferable. As the polyhydric alcohol and its derivative, there are glycerol, ethylene glycol, propylene glycol, 1,3-butylene glycol, dipropylene glycol, polyethylene glycol, polypropylene glycol, and these esters or ethers. The fatty acid ester is a higher fatty acid ester, and esters of a higher fatty acid such as myristic acid, palmitic acid, stearic acid or oleic acid, with a lower alcohol ($C_{1-6}$) may be illustrated.

The surfactant may be an anionic surfactant such as polyoxyethylenealkylether phosphate or sodium alkylsulfate, a sorbitan fatty acid ester such as sorbitan sesquioleate, sorbitan trioleate, sorbitan monostearate, sorbitan monolaurate, polyoxyethylene sorbitan stearate, a nonionic surfactant such as polyoxyethylene nonylether, monooxyethylene cetylether or monooxyethylene laurylether, in addition, a cationic surfactant such as benzethonium chloride or benzalkonium chloride, or an amphoteric surfactant.

The gel-type vehicle includes carboxyvinyl polymer, hydroxyethyl cellulose, hydroxypropyl cellulose, methylcellulose, ethylcellulose, carboxymethyl cellulose and the like.

The external preparation for athlete's foot treatment of the invention may contain a percutaneous absorption promoter, and if said percutaneous absorption promoter is one or more compounds in which a percutaneous absorption promoting action of the anti-trichophyton drug is recognized, any compound may be used.

Examples include $C_6$-$C_{20}$ fatty acids, fatty alcohols, fatty acid esters or fatty acid ethers, aromatic organic acids, aromatic alcohols, aromatic organic acid esters or aromatic organic acid ethers, furthermore lactic acid esters, acetic acid esters, monoterpene compounds, sesquiterpene compounds, Azone or Azone derivatives, glycerol fatty acid esters, sorbitan fatty acid esters, polysorbates, polyethylene glycol fatty acid esters, polyoxyethylene hydrogenated castor oils and sucrose fatty acid esters. Fatty acid esters and fatty alcohols are preferable, in particular, isopropyl miristate, isopropyl palmitate, sorbitan monooleate and oleyl alcohol are preferable.

Further, the external preparation for athlete's foot treatment of the invention may contain an antioxidant, an antiseptic agent, a preservative, a moisturizing agent, a chelate agent and other additive which are usually blended in a skin external preparation.

In the following, the invention is explained in more detail by the examples. The invention, however, is not limited to these examples, and various changes may be made without departing from the spirit of the invention. Further, in the examples, '%' means '% by mass' unless otherwise specified.

EXAMPLES 1-6

Aerosol Preparations (Preparation Method for Aerosol Preparations)

A solid ingredient was dissolved in ethanol, and to this was added with other ingredients to prepare a raw solution. The raw solution and a propellant were filled in an aerosol can to obtain the aerosol preparations of the examples 1-6.

TABLE 1

(Examples of aerosol preparations)

| Composition | Examples | | |
| --- | --- | --- | --- |
| | 1 | 2 | 3 |
| Butenafine hydrochloride | 1 | 0.5 | 1 |
| Diphenhydraminehydrochloride | 0 | 0.2 | 0.2 |
| Chlorpheniraminemaleate | 0 | 0.5 | 0.5 |
| Glycyrrhetinic acid | 0 | 0 | 0.2 |
| 1-Menthol | 2 | 1 | 3 |
| Ethanol | 45 | 50 | 55 |
| Isopropyl myristate | 4 | 4 | 8 |
| 1,3-Butylene glycol | 16 | 20 | 12 |
| Purified water | 32 | 21.8 | 20.1 |
| Raw liquid in total | 100 | 100 | 100 |
| Above raw liquid's amount | 50 | 30 | 35 |
| Dimethyl ether | 30 | 50 | 25 |
| LP gas | 20 | 20 | 40 |
| Aerosol in total | 100 | 100 | 100 |

TABLE 2

| Composition | Examples | | |
| --- | --- | --- | --- |
| | 4 | 5 | 6 |
| Butenafine hydrochloride | 5 | 0.5 | 1 |
| Lidocaine | 0 | 1.5 | 0.5 |
| Diphenhydraminehydrochloride | 0 | 0.5 | 0.5 |
| Dipotassium glycyrrhetinate | 0 | 0 | 0.2 |
| Allantoin | 0.2 | 1.5 | 0 |
| 1-Menthol | 2 | 1 | 3 |
| Ethanol | 25 | 60 | 50 |
| Isopropyl myristate | 4 | 4 | 8 |
| Polyethylene glycol 200 | 27 | 8 | 13 |
| Purified water | 36.8 | 23 | 23.8 |
| Raw liquid in total | 100 | 100 | 100 |
| Above raw liquid's amount | 50 | 30 | 35 |
| Dimethyl ether | 30 | 50 | 25 |
| LP gas | 20 | 20 | 40 |
| Aerosol in total | 100 | 100 | 100 |

(Preparation Method for Creams)

As to a preparation method for a cream, an aqueous phase and an oil phase were each heated at 80° C., mixed and emulsified under a sufficient stirring. Then, the emulsion was cooled under stirring to room temperature to obtain the creams of the examples 7-9.

TABLE 3

(Examples of creams)

| Composition | Examples | | |
|---|---|---|---|
| | 7 | 8 | 9 |
| Oil phase | | | |
| Butenafine hydrochloride | 2 | 1 | 1 |
| Lidocaine | | 0.1 | |
| Diphenhydramine | | 5 | |
| Glycyrrhetinic acid | 5 | | 0.5 |
| 1-Menthol | 1 | 3 | 2 |
| Liquid paraffin | 10 | 10 | 8 |
| Isopropyl myristate | 10 | 5 | 2 |
| Cetanol | 2 | | 3 |
| Stearyl alcohol | 2 | 9 | 3 |
| Polyoxyethylene cetyl ether | 2 | | 4 |

TABLE 3-continued (Examples of creams)

| Composition | Examples | | |
|---|---|---|---|
| | 7 | 8 | 9 |
| Polyoxyethylene sorbitan stearate | | 5 | |
| Carboxyvinyl polymer | | 1.5 | |
| Aqueous phase | | | |
| Lidocaine hydrochloride | | 0.5 | |
| Dibucaine hydrochloride | | | 0.5 |
| Chlorpheniramine hydrochloride | | 0.05 | |
| Chlorpheniramine maleate | | | 0.5 |
| Diethanolamine | 0.2 | 0.2 | 0.2 |
| Methylparaben | 0.2 | 0.2 | 0.2 |
| Purified water | balance | balance | balance |
| Total | 100 | 100 | 100 |

(Preparation Method for Liquid Preparations)

As to a preparation method for a liquid preparation, an active ingredient was dissolved in ethanol, and added to other ingredients to obtain the liquid preparation of the examples 10-17 and the comparative examples 1-3.

TABLE 4

Examples of Liquid Preparations

| Composition | Example 10 | Example 11 | Example 12 | Example 13 | Example 14 | Example 15 |
|---|---|---|---|---|---|---|
| Butenafine hydrochloride | 1.0 | 1.0 | 1.0 | 1.0 | 1.0 | 1.0 |
| Dibucaine hydrochloride | 0.5 | 0.5 | 0.5 | 0.5 | 0.5 | 0.5 |
| Chlorpheniramine maleate | 0.5 | 0.5 | 0.5 | 0.5 | 0.5 | 0.5 |
| Glycyrrhetinic acid | 0.2 | 0.2 | 0.2 | 0.2 | 0.2 | 0.2 |
| Isopropylmethylphenol | 0 | 0 | 0 | 0 | 0 | 0 |
| 1-Menthol | 1 | 2 | 3 | 0 | 0 | 0 |
| MP20H | 0 | 0 | 0 | 0.5 | 1.0 | 2.0 |
| Propylene carbonate | 10 | 10 | 10 | 10 | 10 | 10 |
| Ethanol | 30 | 30 | 30 | 30 | 30 | 30 |
| Sodium hyaluronate | 0.01 | 0.01 | 0.01 | 0.01 | 0.01 | 0.01 |
| Purified water | balance | balance | balance | balance | balance | balance |
| Total | 100 | 100 | 100 | 100 | 100 | 100 |

| Composition | Example 16 | Example 17 | Comparative example 1 | Comparative example 2 | Comparative example 3 |
|---|---|---|---|---|---|
| Butenafine hydrochloride | 1.0 | 1.0 | 1.0 | 1.0 | 1.0 |
| Dibucaine hydrochloride | 0.5 | 0.5 | 0.5 | 0.5 | 0.5 |
| Chlorpheniramine maleate | 0.5 | 0.5 | 0.5 | 0.5 | 0.5 |
| Glycyrrhetinic acid | 0.2 | 0.2 | 0.2 | 0.2 | 0.2 |
| Isopropylmethylphenol | 0 | 0.5 | 0 | 0 | 0 |
| 1-Menthol | 0 | 2 | 0 | 0 | 0 |
| MP20H | 4.0 | 0 | 0 | 0.1 | 0.2 |
| Propylene carbonate | 10 | 10 | 10 | 10 | 10 |
| Ethanol | 30 | 30 | 30 | 30 | 30 |
| Sodium hyaluronate | 0.01 | 0.01 | 0.01 | 0.01 | 0.01 |
| Purified water | balance | balance | balance | balance | balance |
| Total | 100 | 100 | 100 | 100 | 100 |

MP20H: 3-1-Menthoxypropane-1,2-diol

TEST EXAMPLE 1

Sensory Test

The preparations of the examples 10-12 and the comparative example 1 were applied to 20 patients with a skin fungus disease, showing the number of persons who got the refreshing feeling and the efficacy feeling (in particular, alleviation of itch).

TABLE 5

Sensory test

|  | Example 10 | Example 11 | Example 12 | Comparative example 1 |
|---|---|---|---|---|
| Refreshing feeling | 12 persons/ 20 persons | 14 persons/ 20 persons | 17 persons/ 20 persons | 8 persons/ 20 persons |
| Efficacy feeling (alleviation of itch) | 5 persons/ 20 persons | 7 persons/ 20 persons | 10 persons/ 20 persons | 2 persons/ 20 persons |

TEST EXAMPLE 2

Evaluation of Antibacterial Action by Halo Test

Test Method

1. The test bacteria (*Staphylococus aureus, Candida albicans*) were inoculated to a SCD agar culture medium cooled to an appropriate temperature after a high-pressure wet sterilization, adjusting the bacterial count to about $10^6$/mL.

2. The test bacteria incubated in 1. were thinly applied to the SCD agar culture medium formed beforehand into a multilayer, cooled and fixed at room temperature.

3. 50 μL of the following samples were applied to a sterilized paper disc (diameter: 8 mm) for an antibiotic test, which was placed on the culture medium of 2.

4. 3. was incubated at 35° C. for 24-48 hours, and the presence or the absence of a growth inhibition ring which occurred around the paper disc was observed.

Test Samples

A liquid, in which butenafine hydrochloride as an antitrichophyton drug and only 1-menthol as an auxiliary agent were blended, was prepared on an experimental basis (the below formula), and the antibacterial actions against *Staphylococus aureus, Candida albicans* were evaluated. The results are shown in Table 6.

The blend amount of 1-menthol was set in 7 classes in the range of 0-4%.

Test formula of liquid preparation for athlete's foot treatment

Butenafine hydrochloride: 1%

1-Menthol: 0-4%

Macrogol 400: 20%

Ethanol: 30%

Purified water: Residual quantity

TABLE 6

Results

| | Observation results of inhibition ring (diameter of inhibition ring in parentheses) | |
|---|---|---|
| | Test bacteria: *Staphylococcus aureus* | Test bacteria: *Candida albicans* |
| Butenafine hydrochloride: 1% L-Menthol: 0% | Absence of inhibition ring | Absence of inhibition ring |
| Butenafine hydrochloride: 1% L-Menthol: 0.1% | Absence of inhibition ring | Absence of inhibition ring |
| Butenafine hydrochloride: 1% L-Menthol: 0.2% | Absence of inhibition ring | Absence of inhibition ring |
| Butenafine hydrochloride: 1% L-Menthol: 0.5% | Absence of inhibition ring | Presence of inhibition ring (10 mm) |
| Butenafine hydrochloride: 1% L-Menthol: 1% | Presence of inhibition ring (9 mm) | Presence of inhibition ring (10 mm) |
| Butenafine hydrochloride: 1% L-Menthol: 2% | Presence of inhibition ring (10 mm) | Presence of inhibition ring (12 mm) |
| Butenafine hydrochloride: 1% L-Menthol: 4% | Presence of inhibition ring (10 mm) | Presence of inhibition ring (14 mm) |

The antibacterial action was confirmed by blend of not less than 0.5% against *Candida albicans* and not less than 1% against *Staphylococus aureus*.

The evaluation of the antibacterial action by Halo test was carried out by the formulas in the examples 13-17 and the comparative examples 1-3, described in Table 4. The test method is same with that in the test example 2, and the results are shown as follows.

TABLE 7

Results

| | Observation results of inhibition ring (diameter of inhibition ring in parentheses) | |
|---|---|---|
| | Test bacteria: *Staphylococcus aureus* | Test bacteria: *Candida albicans* |
| Comparative example 1 | Absence of inhibition ring | Absence of inhibition ring |
| Comparative example 2 | Absence of inhibition ring | Absence of inhibition ring |
| Comparative example 3 | Absence of inhibition ring | Absence of inhibition ring |
| Example 13 | Presence of inhibition ring (11 mm) | Presence of inhibition ring (11 mm) |
| Example 14 | Presence of inhibition ring (13 mm) | Presence of inhibition ring (13 mm) |
| Example 15 | Presence of inhibition ring (14 mm) | Presence of inhibition ring (15 mm) |
| Example 16 | Presence of inhibition ring (18 mm) | Presence of inhibition ring (16 mm) |
| Example 17 | Presence of inhibition ring (14.5 mm) | Presence of inhibition ring (16 mm) |

The antibacterial action against *Staphylococus aureus* and *Candida albicans* was confirmed in the concentration of not less than 0.5% of 3-l-menthoxypropane-1,2-diol. In addition, in the formula in which isopropylmethylphenol and 1-menthol were blended in combination, it was also confirmed to be able to carry out effectively the suppression of *Staphylococus aureus* and *Candida albicans*.

INDUSTRIAL APPLICABILITY

By using an external preparation for athlete's foot treatment containing an anti-trichophyton drug and a compound suppressing the growth of *Staphylococus aureus* and *Candida albicans* as an essential ingredient, it becomes possible to reduce effectively not only *Trichophyton* but also other fungi such as *Candida albicans* and a skin habitual bacteria such as *Staphylococus aureus*, and therefore, the application to a wide-ranging use such a therapy for a fungus infectious disease or the like can be made.

What is claimed is:

1. An external preparation for athlete's foot treatment, comprising 0.1-10% by mass of butenafine hydrochloride blended with 1-5% by mass of 1-menthol, dibucaine hydrochloride, chlorpheniramine maleate and glycyrrhetinic acid.

2. The external preparation according to claim 1 wherein 0.1-10% by mass of butenafine hydrochloride, 1-5% by mass of 1-menthol, 0.01-5.0% by mass of dibucaine hydrochloride, 0.05-5.0% by mass of chlorpheniramine maleate and 0.05-10.0% by mass of glycyrrhetinic acid are blended.

* * * * *